US006225480B1

(12) United States Patent
Tanaka et al.

(10) Patent No.: US 6,225,480 B1
(45) Date of Patent: May 1, 2001

(54) SULPHONYL COMPOUNDS FOR USE AS LINKERS IN SOLID PHASE AND COMBINATORIAL SYNTHESIS

(75) Inventors: Akito Tanaka, Tsukuba; Hideo Tsutsumi, Toyonaka, both of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/331,580

(22) PCT Filed: Dec. 17, 1997

(86) PCT No.: PCT/JP97/04647

§ 371 Date: Jun. 30, 1999

§ 102(e) Date: Jun. 30, 1999

(87) PCT Pub. No.: WO98/29386

PCT Pub. Date: Jul. 9, 1998

(30) Foreign Application Priority Data

Dec. 30, 1996 (AU) .................................................. P04405

(51) Int. Cl.[7] .................................................. C07D 311/04
(52) U.S. Cl. ........................... 549/398; 435/7.1; 435/7.2; 436/501; 436/518; 530/331; 530/332; 530/333; 530/334; 530/335; 530/336
(58) Field of Search ...................... 435/7.1, 7.2; 436/501, 436/518; 530/331–336; 549/398

(56) References Cited

U.S. PATENT DOCUMENTS 3,720,709 * 3/1973 Sprague et al. ........................ 260/519

OTHER PUBLICATIONS

Rabanal et al. A New Fluorene–Derived Anchor for Solid Phase Synthesis of Protected Peptides. Tet. Lett., vol. 33, No. 13, pp. 1775–1778, Mar. 1992.*

* cited by examiner

*Primary Examiner*—Jyothsna Venkat
*Assistant Examiner*—Maurie E. Garcia
(74) *Attorney, Agent, or Firm*—Oblon, Spivak, McClelland, Maier & Neustadt, P.C.

(57) ABSTRACT

The present invention relates to a linker shown by the following formula (I):

$$X\text{—}SO_2\text{—}R^1\text{—}(A)_m\text{—}R^2 \qquad (I)$$

wherein $R^1$ is a group of the formula (A):

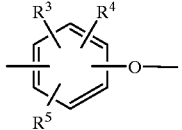

formula (A)

[wherein $R^3$, $R^4$ and $R^5$ are the same or different hydrogen, etc], etc,
  $R^2$ is a group which can form a chemical bond to a resin which may be protected by a conventional protective group,
  A is lower alkylene, etc,
  X is a leaving group, and
  m is an integer of 0 or 1,
with proviso that A is $(C_2\text{–}C_6)$alkylene, and
  m is an integer of 1,
  when $R^1$ is a group of the formula (A).

7 Claims, No Drawings

SULPHONYL COMPOUNDS FOR USE AS LINKERS IN SOLID PHASE AND COMBINATORIAL SYNTHESIS

BACKGROUND OF THE INVENTION

1. Field of the Invention

The present invention relates to the field of the solid phase chemistry. More particularly, the present invention provides a linker for solid phase and combinatorial synthesis of an organic compound containing —NH— group in its molecule (e.g. amidino group).

2. Description of the Background

Chemical methods have been developed recently for the synthesis of combinatorial libraries of various organic compounds such as peptides, benzodiazepines, oligosaccharides, etc. Solid phase methods are often employed to synthesize the combinatorial libraries because it offers advantages over traditional solution-based methods, for examples, a) excess reagents and soluble by-products can be simply removed by resin washing; b) the technique is readily amenable to automation, enabling many compounds to be prepared simultaneously; c) resin bound toxic or hazardous compounds can be handled safely without risk to users or the environment. In combinatorial synthesis using the solid phase synthesis, it is very important to choose a "suitable linker" in accordance with the object compound to be synthesized.

Up to now, however, a linker efficiently available for amidino group in the solid phase synthesis has not been known. Therefore, such linker is desired.

DETAILED DESCRIPTION OF THE PREFERRED EMBODIMENTS

The linker of the present invention can be shown by the following formula (I):

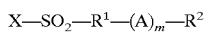

X—SO$_2$—R$^1$—(A)$_m$—R$^2$    (I)

wherein

R$^1$ is a group of the formula (A), (B), (C), (D) and (E):

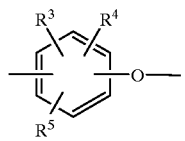

formula (A)

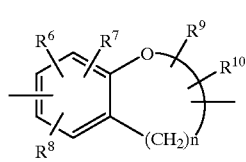

formula (B)

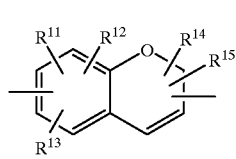

formula (C)

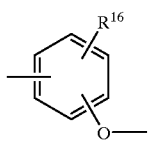

formula (D)

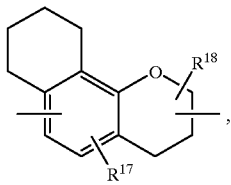

formula (E)

[wherein R$^3$, R$^4$, R$^5$, R$^6$, R$^7$, R$^8$, R$_9$, R$^{10}$, R$^{11}$, R$^{12}$, R$^{13}$, R$^{14}$, R$^{15}$, R$^{16}$, R$^{17}$ and R$^{18}$ are the same or different hydrogen, lower alkyl or lower alkoxy, and n is an integer of 1 to 3], R$^2$ is a group which can form a chemical bond to a resin which may be protected by a conventional protective group, A is lower alkylene or a group of the formula:

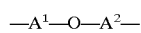

—A$^1$—O—A$^2$—

(wherein A$^1$ and A$^2$ are each lower alkylene),

X is a leaving group, and m is an integer of 0 or 1, with proviso that A is (C$_2$–C$_6$)alkylene, and m is an integer of 1, when R$^1$ is a group of the formula (A).

The linker of the present invention can be prepared by the following reaction scheme.

Process 1

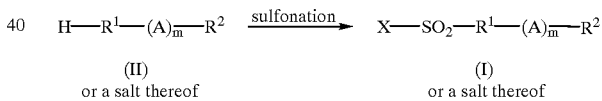

H—R$^1$—(A)$_{\overline{m}}$—R$^2$  $\xrightarrow{\text{sulfonation}}$  X—SO$_2$—R$^1$—(A)$_{\overline{m}}$—R$^2$ (II)                                    (I)

or a salt thereof                       or a salt thereof wherein R$^1$, R$^2$, A, X and m are each as defined above.

The sulfonation reaction can be carried out, for example, in accordance with the methods described in Examples in this specification, but not limited thereto, the reaction can be carried out according to the methods known in this field of the art.

The starting compound (II) or a salt thereof can be prepared according to Preparations in this specification or similar manners thereto, for instance. Further, one can prepare the compound (II) or a salt thereof from a known compound in accordance with the known methods in this field of the art.

In the above and following description of the present specification, suitable examples and illustrations of the various definitions which the present invention includes within the scope thereof are explained in detail as follows.

Suitable "salt" may be the conventional ones and include a metal salt such as an alkali metal salt (e.g. sodium salt, potassium salt, etc) and an alkaline earth metal salt (e.g. calcium salt, magnesium salt, etc), an ammonium salt, an organic base salt (e.g. trimethylamine salt, triethylamine salt, pyridine salt, picoline salt, dicyclohexylamine salt, N,N'-dibenzylethylenediamine salt, etc), an organic acid salt (e.g. acetate, trifluoroacetate, maleate, tartrate, fumarate, methanesulfonate, benzenesulfonate, formate, toluenesulfonate, etc), an inorganic acid salt (e.g. hydrochloride, hydrobromide, hydriodide, sulfate, phosphate, etc), a salt with an amino acid (e.g. arginine, aspartic acid, glutamic acid, etc), and the like.

Suitable "lower alkyl" may include straight or branched ones having 1 to 6 carbon atom(s) such as methyl, ethyl, propyl, isopropyl, butyl, t-butyl, pentyl, hexyl, or the like.

Suitable "lower alkylene" may include straight or branched ones having 1 to 6 carbon atom(s) such as methylene, ethylene, trimethylene, 1-methylethylene, tetramethylene, pentamethylene, hexamethylene, or the like.

Suitable "lower alkoxy" may include straight or branched ones having 1 to 6 carbon atom(s) such as methoxy, ethoxy, propoxy, isopropoxy, butoxy, t-butoxy, pentyloxy, hexyloxy, or the like.

Suitable "a group which can form a chemical bond to a resin" may be selected in accordance with the kind of resin (e.g. amino-resin, etc) and the concrete examples thereof can be exemplified as follows (the corresponding resin type is also indicated; <P> means "resin").

| | |
|---|---|
| 1) —COOH | ($H_2$N-<P>) |
| 2) —$NH_2$ | (HOOC-<P>)(Z-$SO_2$-<P>; Z means a leaving group) |
| 3) a leaving group | ($H_2$N-<P>) |
| 4) —C=P$\phi_3$; $\phi$ means "phenyl" | (OHC-<P>) |
| 5) —C=$CH_2$ | (Z-$\phi$-<P>) |
| 6) —C≡CH—X | ((HO)$_2$B-$\phi$-<P>) |
| 7) —CHO | ($\phi_3$P—CH-<P>)($H_2$N-<P>) |
| | (HO—$CH_2$CH(OH)$CH_2$-<P>) |
| 8) —OH | (Z-$CH_2$-<P>) |
| 9) —SH | (Z-$CH_2$-<P>) |
| 10) —Si($CH_3$)$_2$H | ($H_2$C=CH-<P>) |
| 11) —$SO_2$Z | ($H_2$N-<P>) |

Suitable "protected carboxy" may be the conventionally protected carboxy and may include esterified carboxy such as lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc), halo(lower)alkoxycarbonyl (e.g. trichloroethoxycarbonyl, etc) and the like.

Suitable "a leaving group" may include halogen (e.g. fluoro, chloro, bromo, iodo), lower alkoxy as mentioned above, aryloxy (e.g. phenoxy, etc), and the like.

Preferred embodiment of the linker (I) may be as follows.
1. the linker (I) wherein
   $R^1$ is a group of the formula (A) wherein $R^3$, $R^4$ and $R^5$ are each lower alkyl,
   $R^2$ is a group which can form a chemical bond to a resin which may be protected by a conventional protective group,
   A is ($C_2$–$C_4$)alkylene or a group of the formula:

—$A^1$—O—$A^2$—

[wherein $A^1$ and $A^2$ are each ($C_1$–$C_4$)alkylene],
   X is halogen,
   m is an integer of 1,
   in which the more preferred one may be the linker (I) wherein $R^1$ is a group of the formula:

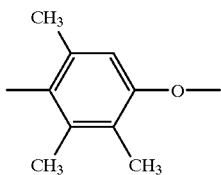

$R^2$ is carboxy or protected carboxy,
   A is trimethylene,
   X is chloro, and
   m is an integer of 1.
2. the linker (I) wherein
   $R^1$ is a group of the formula (B) wherein $R^6$, $R^7$, $R^8$ and $R^9$ are each lower alkyl, $R^{10}$ is hydrogen, and n is an integer of 3,
   $R^2$ is a group which can form a chemical bond to a resin which may be protected by a conventional protective group,
   A is ($C_1$–$C_4$)alkylene or a group of the formula:

—$A^1$—O—$A^2$—

[wherein $A^1$ and $A^2$ are each ($C_1$–$C_4$)alkylene],
   X is halogen, and
   m is an integer of 0 or 1,
   in which the more preferred one may be the linker (I) wherein
   $R^1$ is a group of the formula:

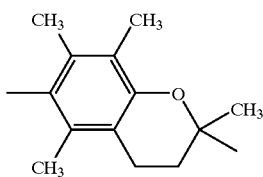

$R^2$ is carboxy or protected carboxy,
   A is methylene or —($CH_2$)$_2$—O—$CH_2$—,
   X is chloro, and
   m is an integer of 1.
3. the linker (I) wherein
   $R^1$ is a group of the formula (B) wherein $R^6$, $R^7$, $R^8$, $R^9$ and $R^{10}$ are each lower alkyl, and n is an integer of 3,
   $R^2$ is a group which can form a chemical bond to a resin which may be protected by a conventional protective group,
   A is ($C_1$–$C_4$)alkylene or a group of the formula:

—$A^1$—O—$A^2$—

[wherein $A^1$ and $A^2$ are each ($C_1$–$C_4$)alkylene],
   X is halogen, and
   m is an integer of 0 or 1,
   in which the more preferred one may be the linker (I) wherein $R^1$ is a group of the formula:

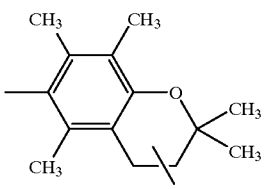

$R^2$ is carboxy or protected carboxy,
X is chloro, and
m is an integer of 0, or
$R^1$ is a group of the formula:

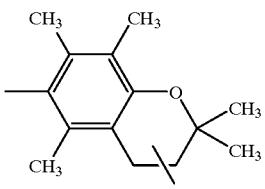

$R^2$ is carboxy or protected carboxy,
A is methylene,
X is chloro, and
m is an integer of 1.
4. the linker (I) wherein
$R^1$ is a group of the formula (C) wherein $R^{11}$, $R^{12}$, $R^{13}$, $R^{14}$ are each lower alkyl, and $R^{15}$ is hydrogen,
$R^2$ is a group which can form a chemical bond to a resin which may be protected by a conventional protective group,
A is $(C_1-C_4)$alkylene or a group of the formula:

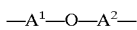

[wherein $A^1$ and $A^2$ are each $(C_1-C_4)$alkylene],
X is halogen,
m is an integer of 1,
in which the more preferred one may be the linker (I) wherein
$R^1$ is a group of the formula:

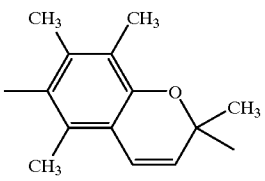

$R^2$ is carboxy or protected carboxy,
A is methylene,
X is chloro, and
m is an integer of 1.
5. the linker (I) wherein
$R^1$ is a group of the formula (D) wherein $R^{16}$ is lower alkyl,
$R^2$ is a group which can form a chemical bond to a resin which may be protected by a conventional protective group, A is $(C_1-C_4)$alkylene or a group of the formula:

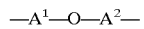

[wherein $A^1$ and $A^2$ are each $(C_1-C_4)$alkylene],
X is halogen,
m is an integer of 1,
in which the more preferred one may be the linker (I) wherein
$R^1$ is a group of the formula:

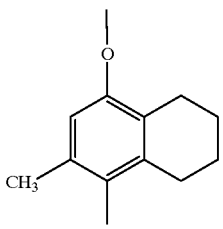

$R^2$ is carboxy or protected carboxy,
A is trimethylene,
X is chloro, and
m is an integer of 1.
6. the linker (I) wherein
$R^1$ is a group of the formula (E) wherein $R^{17}$ and $R^{18}$ are each lower alkyl,
$R^2$ is a group which can form a chemical bond to a resin which may be protected by a conventional protective group,
A is $(C_1-C_4)$alkylene or a group of the formula:

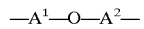

[wherein $A^1$ and $A^2$ are each $(C_1-C_4)$alkylene],
X is halogen,
m is an integer of 1,
in which the more preferred one may be the linker (I) wherein
$R^1$ is a group of the formula:

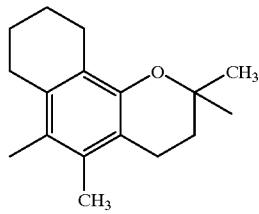

$R^2$ is carboxy or protected carboxy,
A is methylene,
X is chloro, and
m is an integer of 1.

The linker which the present invention provides is the efficient one for the solid phase synthesis of the compound containing —NH— group such as "amidino" group in its molecule (hereinafter referred to as "amine compound" in this specification). Since there are various therapeutically active "amine compound" and so the present invention is very useful in the solid phase synthesis.

Since the compound (I) of the present invention is "linker", the "amine compound" to be used is not limited and the present invention can be applied to any "amine compound" which is useful as the key intermediate in the solid phase synthesis and can form a bond to the linker of the present invention during the solid phase reaction, then can be cleaved after the reaction.

As for said "amine compound", the following compounds can be exemplified, but it is not limited thereto.
1) the compound of the formula:

[wherein $R^a$, $R^b$ and $R^c$ are each a residue of an organic group such as lower alkyl, aryl (e.g. phenyl, naphthyl, anthryl, etc)];
2) the compound of the formula:

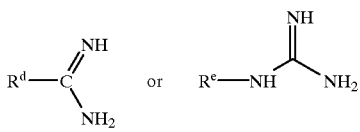

[wherein $R^d$ and $R^e$ are each a residue of an organic group such as lower alkyl, aryl (e.g phenyl, naphthyl, anthryl, etc)];
3) heterocyclic compound containing —NH— moiety such as imidazole or its derivative, indole or its derivative, or the like.

Said "amine compound" can be reacted with the linker of the present invention in a conventional manner to form the compound of the formula:

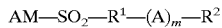

wherein AM is a residue of "amine compound", and
$R^1$, $R^2$, A and m are each as defined above.

As for this compound, the preferred "—$SO_2$—$R^1$—$(A)_m$—$R^2$" moiety can be referred to the ones as exemplified for the linker (I) before.

If "a group which can form a chemical bond to a resin" can also react with said "amine compound", this group can be protected by a conventional protective group in this field of the art. The protective group can be selected depending on the kind of "a group which can form a chemical bond to a resin".

During the solid phase synthesis, the linker of the present invention, "amine compound" and "resin" form the following structure.

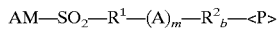

wherein $R^2_b$ is a chemical bond, <P> is resin, and
AM, $R^1$, $R_2$, A and m are each as defined above.

In order to show said usefulness, we describe later in this specification the concrete examples (References) which show how the linker of the present invention contributes to the solid phase synthesis of the derivatives of "amine compound" using "benzamidine", etc as the representative compound.

The following Preparations, Examples and References are given only for the purpose of illustrating the present invention in more detail.
Preparation 1

A mixture of 2,3,5-trimethylphenol (10.0 g), ethyl 4-bromobutyrate (12.6 ml), potassium carbonate (12.2 g), and dimethylformamide (DMF, 100 ml) was stirred at room temperature overnight. The reaction mixture was poured into a mixture of ethyl acetate (AcOEt) and water. The separated organic phase was washed with a saturated aqueous solution of sodium hydrocarbonate (sat. $NaHCO_3$aq.), water, and brine, and was dried over magnesium sulfate ($MgSO_4$). After evaporation, the resulting residue was purified by chromatography over silica gel ($CHCl_3$ as eluent) to give ethyl 4-(2,3,5-trimethylphenoxy)butyrate (16.35 g) as an oil compound.

IR (Neat): 2937, 2870, 1736, 1614, 1583 $cm^{-1}$
$^1$H-NMR (200 MHz, $CDCl_3$, δ): 1.27 (3H, t, J=7.1 Hz), 2.0–2.4 (2H, m), 2.04 (3H, s), 2.22 (3H, s), 2.27 (3H, s), 2.50 (2H, t, J=7.4 Hz), 3.97 (2H, t, J=7.4 Hz), 4.14 (2H, q, J=7.1 Hz), 6.51 (1H, s), 6.60 (1H, s)
MASS spectrum m/e: 251 (M+H$^+$)

EXAMPLE 1

A mixture of chlorosulfonic acid (4.78 ml) and $CH_2Cl_2$ (25 ml) was added dropwise into a mixture of ethyl 4-(2,3,5-trimethylphenoxy)butyrate (6.00 g) and dichloromethane ($CH_2Cl_2$, 500 ml) under ice-water cooling over 10 minutes, and was stirred at room temperature for 2.5 hours. The reaction mixture was poured into a mixture of ice and sat. $NaHCO_3$aq. The separated organic phase was washed with sat. $NaHCO_3$aq., water, and brine, and was dried over $MgSO_4$. After filtration, the filtrate was evaporated to give 4-(3-ethoxycarbonylpropoxy)-2,3,6-trimethylbenzenesulfonyl chloride (16.35 g) as an oil compound.

IR (Neat): 1983, 2940, 1733, 1581, 1558, 1465 $cm^{-1}$
$^1$H-NMR (200 MHz, $CDCl_3$, δ): 1.27 (3H, t, J=7.2 Hz), 2.0 2.4 (2H, m), 2.04 (3H, s), 2.55 (2H, t, J=7.1 Hz), 2.67 (3H, s), 2.71 (3H, s), 4.0–4.2 (4H, m), 6.65 (1H, s)
Reference 1

1N NaOH (6.43 ml) was added into a mixture of benzamidine hydrochloride (1.00 g) and acetone (25 ml) under ice-water cooling, and then a mixture of 4-(3-ethoxycarbonylpropoxy)-2,3,6-trimethylbenzenesulfonyl chloride (3.36 g) and acetone (5 ml) was added dropwise thereto over 10 minutes. The reaction mixture was stirred at room temperature for 2 hours. The reaction mixture was concentrated by $N_2$ flow to remove the excess of solvents, and was poured into a mixture of water and AcOEt. The separated organic phase was washed with sat. $NaHCO_3$aq., water, and brine, and was dried over $MgSO_4$. After evaporation, the resulting residue was purified by chromatography over silica gel ($CHCl_3$-methanol (MeOH) as eluent) to give N-[4-(3-ethoxycarbonylpropoxy)-2,3,6-trimethylbenzenesulfonyl]benzamidine (1.39 g) as an oil compound.

IR (Neat): 3425, 3328, 1729, 1633, 1585, 1537 $cm^{-1}$
$^1$H-NMR (200 MHz, $CDCl_3$, δ): 1.29 (3H, t, J=7.1 Hz), 2.0–2.4 (2H, m), 2.10 (3H, s), 2.52 (2H, t, J=7.1 Hz), 2.66 (3H, s), 2.73 (3H, s), 4.03 (2H, t, J=6.0 Hz), 4.14 (2H, q, J=7.1 Hz), 6.55 (1H, s), 7.3–7.6 (3H, m), 7.77 (2H, d, J=6.9 Hz)
MASS spectrum m/e: 433 (M+H$^+$)
Reference 2

A mixture of N-[4-(3-ethoxycarbonylpropoxy)-2,3,6-trimethylbenzenesulfonyl]benzamidine (0.39 g), 1N NaOH (1.80 ml), and ethanol (EtOH, 1 ml) was stirred at room temperature overnight. The reaction mixture was poured into a mixture of ethyl acetate (AcOEt) and dil. HCl. The separated organic phase was washed with water and brine, and was dried over magnesium sulfate ($MgSO_4$). After evaporation, the resulting residue was dissolved with AcOEt. Dicyclohexylamine (0.18 ml) was added thereto, and was evaporated in vacuo. The resulting precipitate was washed with diethyl ether (Et$_2$O) to give N-[4-(3-carboxypropoxy)-2,3,6-trimethylbenzenesulfonyl] benzamidine dicyclohexylamine salt (16.35 g).

mp: 157–160° C.

IR (KBr): 3371, 2939, 2859, 1618, 1552, 1446 cm$^{-1}$ $^1$H-NMR (200 MHz, CDCl$_3$, δ): 1.0–3.0 (26H, m), 2.14 (3H, s), 2.38 (2H, t, J=7.0 Hz), 2.65 (3H, s), 2.71 (3H, s), 4.03 (2H, t, J=6.3 Hz), 6.55 (1H, s), 6.59 (1H, brs), 7.2–7.6 (6H, m), 7.78 (2H, d, J=7.1 Hz)

MASS spectrum m/e: 405 (M+H$^+$ of free)

Anal. Calcd. for C$_{32}$H$_{47}$N$_3$O$_5$S: C, 65.61; H, 8.09; N,7.17.

Found: C, 65.65; H, 8.44; N,6.71.

Reference 3

N-[4-(3-Carboxypropoxy)-2,3,6-trimethylbenzenesulfonyl]benzamidine dicyclohexylamine salt (586 mg) was dissolved with a mixture of dil. HCl and CH$_2$Cl$_2$. The separated organic layer was washed with water and brine, and dried over MgSO$_4$. After filtration, 1-(3-dimethylamino-propyl)ethylcarbodiimide hydrochloride (211 mg) and 1-hydroxybenzotriazole (149 mg) were added to the filtrate. The reaction mixture was mixed with aminomethylated polystyrene resin (0.78 mmol/g, 586 mg), was shook by N$_2$ bubbling at room temperature for 2.5 hours. The Ninhydrin test on the reaction resin was negative at the end of the reaction. The resin was washed 5 times with CH$_2$Cl$_2$. After dried by N$_2$ flow, 20% acetic anhydride in CH$_2$Cl$_2$ (50 ml) was added thereto to complete capping of the resin. The resin was washed with CH$_2$Cl$_2$ 5 times, and dried by N$_2$ flow and in vacuo to give "compound 1" (771 mg).

compound 1

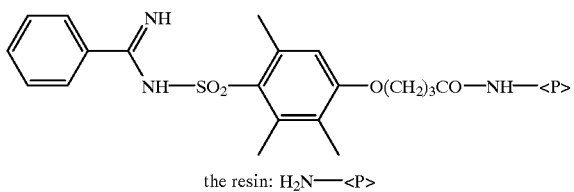

the resin: H$_2$N—<P>

Reference 4

The "resin 1" (187 mg) was mixed with a mixture of m-cresol (0.04 ml), thioanisole (0.24 ml), 1,2-ethanedithiol (0.12 ml), trimethylsilylbromide (0.27 ml), and trifluoroacetic acid (TFA, 1.3 ml). The reaction mixture was heated at 80° C. for 13 hours. After filtration, the resin was washed with TFA 3 times. The combined filtrate was concentrated by N$_2$ flow, and was poured into Et$_2$O (6 ml), which resulted in white precipitation. The mixture was cooled by dry-ice for 1 hour, and was centrifuged at 3000 rpm for 3 minutes. This washing operation was repeated twice. The resulting precipitate was dried to give benzamidine trifluoroacetate (13.2 mg).

mp: 214° C. (decomp.)

Anal. Calcd. for C$_7$H$_8$N$_2$.CF$_3$COOH.0.6 H$_2$O: C, 44.13; H, 4.20; N, 11.43.

Found: C, 44.30; H, 3.99; N, 11.05.

The retention time of HPLC under the following conditions of the product was consistent with an authentic sample.

HPLC conditions:
Column; YMC-PACK R-ODS-15 S-15 120A ODS (YMC Co., Ltd.),
4.6φ×250 mm;
Flow, 1 ml/min;
Detection, 254 nm;

Retention time, 6.74 min;

Elution program was shown in Table 1.

TABLE 1

| Time program for the HPLC study | | | | | |
|---|---|---|---|---|---|
| 0 | 6.00 | 6.01 | 8.00 | 8.01 | minute |
| 5 | 5 | 80 | 80 | 5 | % CH$_3$CN in 0.1 % TFA aq. |

Preparation 2

A mixture of 4-(2,3,5-trimethylphenoxy)butyrate (9.09 g), 1N NaOH (58 ml), and EtOH (80 ml) was stirred at room temperature overnight. The reaction mixture was poured into a mixture of Et$_2$O and water. The separated water phase was washed with Et$_2$O, and was acidified by 6N HCl. After extraction by AcOEt, the AcOEt was washed with water and brine, and dried over MgSO$_4$, and then evaporated. The resulting precipitate was collected by filtration, and dried to give 4-(2,3,5-trimethylphenoxy)butyric acid (4.91 g).

mp: 90–93° C.

IR (KBr): 2913, 1712, 1581 cm$^{-1}$ $^1$H-NMR (200 MHz, CDCl$_3$, δ): 1.94 (2H, tt, J=7.1 and 6.3 Hz), 2.01 (3H, s), 2.15 (3H, s), 2.01 (3H, s), 3.40 (2H, t, J=7.1 Hz), 3.91 (2H, t, J=6.3 Hz), 6.56 (1H, s), 6.57 (1H, s), 12.12 (1H, br s)

MASS spectrum m/e: 223 (M+H$^+$)

Preparation 3

A mixture of 4-(2,3,5-trimethylphenoxy)butyric acid (4.82 mg) dimethylaminopyridine (DMAP, 0.26 g), 2,2,2-trichloroethanol (2.50 ml), 1-(3-dimethylaminopropyl) ethylcarbodiimide hydrochloride (4.57 g) and CH$_2$Cl$_2$ was stirred at room temperature overnight. The reaction mixture was poured into a mixture of AcOEt and water. The separated AcOEt was washed with dil. HCl, sat. NaHCO$_3$, water, and brine, and dried over MgSO$_4$, and then evaporated to give 2,2,2-trichloroethyl 4-(2,3,5-trimethylphenoxy) butyrate (8.11 g) as an oil compound.

IR (KBr): 2925, 1754, 1612, 1581 cm$^{-1}$ $^1$H-NMR (200 MHz, CDCl$_3$, δ): 2.01 (3H, s), 2.04 (2H, m), 2.15 (3H, s), 2.04 (3H, s), 2.67 (2H, t, J=7.1 Hz), 3.97 (2H, t, J=6.3 Hz), 6.81 (2H, br s)

MASS spectrum m/e: 353 (M$^+$)

EXAMPLE 2

The following compound was obtained according to a similar manner to that of Example 1.

4-[3-(2,2,2-Trichloroethoxy)carbonylpropoxy]-2,3,6-trimethylbenzenesulfonyl chloride (6.40 g) as an oil compound.

IR (Neat): 2939, 1756, 1681, 1606, 1583, 1556 cm$^{-1}$ $^1$H-NMR (200 MHz, CDCl$_3$, δ) 2.01 (3H, s), 2.04 (2H, m), 2.15 (3H, s), 2.04 (3H, s), 2.67 (2H, t, J=7.1 Hz), 3.97 (2H, t, J=6.3 Hz), 6.84 (1H, s)

MASS spectrum m/e: 451 (M-H$^+$)

Reference 5

The following compound was obtained according to a similar manner to that of Reference 1.

4-Ethoxycarbonylpropoxy-N-{4-[3-(2,2,2-trichloroethoxycarbonyl)propoxy]-2,3,6-trimethylbenzenesulfonyl}benzamidine (3.28 g) as an oil compound.

$^1$H-NMR (200 MHz, CDCl$_3$, δ): 1.17 (3H, t, J=7.1 Hz), 1.8–2.1 (4H, m), 2.22 (3H, s), 2.4–2.8 (10H, m), 4.0–4.2 (6H, m), 4.90 (2H, s), 6.75 (1H, s), 6.99 (2H, d, J=8.9 Hz), 7.82 (2H, d, J=8.9 Hz), 7.83 (1H, br s), 8.76 (1H, s)

MASS spectrum m/e: 667 (M+H$^+$)

Reference 6

Zn powder (0.32 g) was added to a mixture of 4-ethoxycarbonylpropoxy-N-{4-[3-(2,2,2-trichloroethoxycarbonyl)propoxy]-2,3,6-trimethylbenzenesulfonyl}benzamidine (0.65 g), water (2 ml), and AcOH (18 ml) under ice-water cooling. The reaction mixture was stirred at room temperature for 3.25 hours, and then evaporated. The resulting precipitate was removed by filtration, and was washed with AcOEt and isopropyl ether (IPE). The filtrate, AcOEt, and IPE were combined, and then washed with water. The organic phase was dried over $MgSO_4$, and evaporated. The resulting residue was purified by chromatography over silica gel ($CHCl_3$-MeOH as eluent) to give 4-ethoxycarbonylpropoxy-N-[4-(3-carboxypropoxy)-2,3,6-trimethylbenzenesulfonyl]benzamidine (0.17 g) as an oil compound.

IR (Neat): 3424, 3330, 3243, 2973, 1725, 1720, 1635 $cm^{-1}$ $^1$H-NMR (200 MHz, $CDCl_3$, δ): 1.17 (3H, t, J=7.1 Hz), 1.8–2.1 (4H, m), 2.22 (3H, s), 2.4–2.8 (10H, m), 4.0–4.2 (6H, m), 4.90 (2H, s), 6.75 (1H, s), 6.99 (2H, d, J=8.9 Hz), 7.82 (2H, d, J=8.9 Hz), 7.83 (1H, br s), 8.76 (1H, s)

MASS spectrum m/e: 535 ($M+H^+$)

Anal. Calcd. for $C_{26}H_{34}N_2O_8S \cdot 1/4H_2O$: C, 57.92, H; 6.45; N; 5.20.

Found: C, 57.93; H, 6.45; N; 5.06.

Reference 7

A mixture of 4-ethoxycarbonylpropoxy-N-[4-(3-carboxypropoxy)-2,3,6-trimethylbenzenesulfonyl]benzamidine (1.00 g), 1-(3-dimethylaminopropyl)ethylcarbodiimide hydrochloride (0.39 g), aminomethylated polystyrene resin (ArgoGel® 0.41 mmol/g, 1.14 g), 1-hydroxybenzotriazole (149 mg), $CH_2Cl_2$ (5 ml), and DMF (5 ml) was shooked by $N_2$ bubbling at room temperature for 2 hours. The Keiser test on the reaction resin was negative at the end of the reaction. The resin was washed 5 times with $CH_2Cl_2$ and DMF, and dried by $N_2$ flow to give the following "compound 2", which was used in the next reaction without further treatment.

Reference 8

A mixture of the above resin (2, assumed 0.47 mmol according to Reference 7), 1N NaOH (1.56 ml), and EtOH (10 ml) was shook by $N_2$ bubbling room temperature overnight. The end of the reaction was determined by solid phase $^1$H-NMR on the resin using nanoprobe (Varian Unity plus 300). The resin was washed with EtOH, water, 0.5N HCl, $CH_2Cl_2$, and DMF, and dried by $N_2$ flow to give the following "compound 3", which was used in the next reaction without further treatment.

compound 3

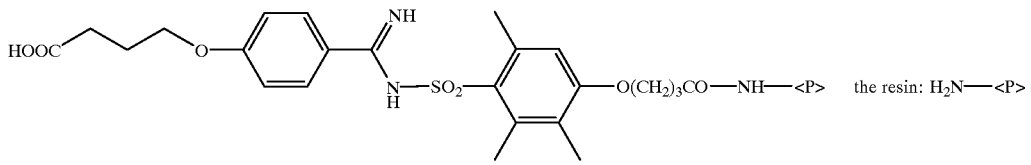

Reference 9

A mixture of the above resin (3, assumed 0.47 mmol according to Reference 7), H-Asp(OtBu)ValOtBu (0.53 g), 1-(3-dimethylaminopropyl)ethylcarbodiimide hydrochloride (0.30 g), 1-hydroxybenzotriazole (0.21 g), and $CH_2Cl_2$ (15 ml) was shooked by $N_2$ bubbling at room temperature for 9 hours. The end of the reaction was determined by solid phase $^1$H-NMR on the resin using nanoprobe (Varian Unity plus 300). The resin was washed with $CH_2Cl_2$, and DMF, and dried by $N_2$ flow to give the following "compound 4", which was used in the next reaction without further treatment.

compound 2

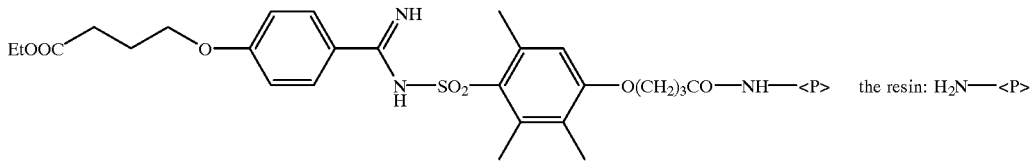

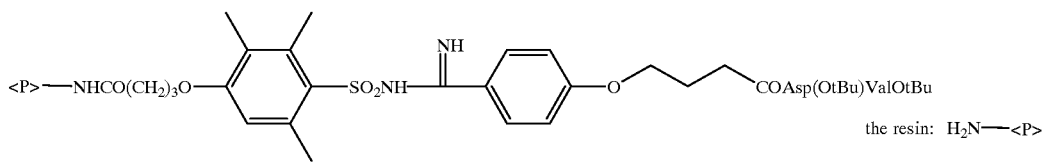

compound 4 the resin: $H_2N$—<P>

Reference 10

The resin 4 (assumed 0.47 mmol according to Reference 7), was mixed with a mixture of trifluoromethanesulfonic acid (TfOH, 0.8 ml), thioanisole (TA, 0.8 ml), and TFA (7.2 ml). The reaction mixture was stirred under water cooling for 2.5 hours. After filtration, the resin was washed with TFA 3 times. The combined filtrate was concentrated by $N_2$ flow, and was poured into a mixture of water (40 ml) and $Et_2O$ (40 ml). The mixture was adjusted to pH 2.08 by addition of 1N NaOH. The separated water phase was subjected to preparative HPLC under the below conditions to give the following compound 5 (57.0 mg, 56.3% from Reference 7).

mp: 155–158° C.

IR (KBr): 3332, 3118, 1718, 1668, 1614 $cm^{-1}$ $^1$H-NMR (DMSO-$d_6$, δ) 0.84 (6H, d, J=6.7 Hz), 1.8–2.2 (3H, m), 2.30 (2H, t, J=7.3 Hz), 2.3–2.8 (2H, m), 4.0–4.2 (3H, m), 4.65 (1H, m), 7.14 (2H, d, J=8.9 Hz), 7.79 (1H, d, J=8.5 Hz), 7.82 (2H, d, J=8.9 Hz), 8.30 (1H, d, J=7.7 Hz), 9.03 and 9.14 (4H, each s)

MASS spectrum m/e: 437 (M+H$^+$)

Preparative HPLC conditions: Column, YMC-PACK R-ODS-15 S-15 120A ODS (YMC Co., Ltd.), 50φ×250 mm; Elution, 16% $CH_3CN$ in 0.1% TFAaq., Flow, 118 ml/min; Detection, 254 nm; Retention time, 6.5 min.

The purity of the product was confirmed by RP-HPLC under the following conditions, and the retention time was consistent with an authentic sample.

Analytical HPLC conditions: Column, YMC-PACK R-ODS-15 S-15 120A ODS (YMC Co., Ltd), 4.6φ×250 mm; Flow, 1 ml/min; Detection, 254 nm; Retention time, 6.7 min; Elution 18% $CH_3CN$ in 0.1% TFA aq.

compound 5

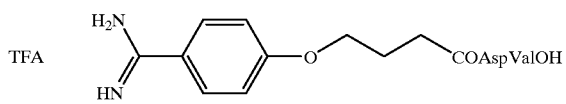

Preparation 4

According to the method of G. Manecke and G. Bourweig (Chem. Ber., 1959, 92, 2958–61), 2-hydroxy-3,4,6-trimethylbenzaldehyde was synthesized from 2,3,5-trimethylphenol.

Preparation 5

A suspension of 2-hydroxy-3,4,6-trimethylbenzaldehyde (16.45 g), diethyl isopropylidenemalonate (20.05 g), and anhydrous potassium carbonate (40.10 g) in dimethylformamide (DMF) (11) was heated at 130–135° C. for 8 hours. After removing the solvent under reduced pressure, the mixture was diluted with water, and extracted with ethyl acetate (AcOEt).

The organic phase was washed with water and brine, dried over magnesium sulfate ($MgSO_4$), and evaporated to give a residue. The residue was purified by chromatography over silica gel (AcOEt-hexane 3:97 as eluent) to give ethyl (2,5,7,8-tetramethyl-2H-chromen-2-yl)acetate as an oil (22.45 g).

bp: 152–153° C. (2 mm)

IR (Neat): 1735, 1608 $cm^{-1}$ $^1$H-NMR (200 MHz, $CDCl_3$, δ): 1.23 (3H, t, J=7.1 Hz), 1.57 (3H, s), 2.07 (3H, s), 2.19 (3H, s), 2.23 (3H, s), 2.67 and 2.71 (2H, ABq, J=14.0 Hz), 4.11 (2H, q, J=7.1 Hz), 5.72 (1H, d, J=9.9 Hz), 6.54 (1H, s), 6.55 (1H, d, J=9.9 Hz)

MASS spectrum m/e: 275 (M+H$^+$), 187 (M$^+$-$CH_2CO_2Et$)

Preparation 6

A solution of ethyl (2,5,7,8-tetramethyl-2H-chromen-2-yl)acetate (20.00 g) in methanol (MeOH) (300 ml) was hydrogenated in the presence of 10% palladium on carbon (50% wet, 4.0 g) in one atmosphere of hydrogen at room temperature for 16 hours. The catalyst was filtered off and MeOH was removed under reduced pressure to give a residue. The residue was purified by chromatography over silica gel (AcOEt-hexane 3:97 as eluent) to give ethyl (2,5,7,8-tetramethylchroman-2-yl)acetate as an oil (18.72 g).

bp: 157–159° C. (2 mm)

IR (Neat): 1732, 1575 $cm^{-1}$ $^1$H-NMR (200 MHz, $CDCl_3$, δ): 1.26 (3H, t, J=7.1 Hz), 1.43 (3H, s), 1.8–2.1 (2H, m), 2.05 (3H, s), 2.16 (3H, s), 2.19 (3H, s), 2.55–2.75 (4H, m), 4.15 (2H, q, J=7.1 Hz), 6.57 (1H, s)

MASS spectrum m/e: 277 (M+H$^+$), 189 (M$^+$—$CH_2CO_2Et$)

Anal. Calcd. for $C_{17}H_{24}O_3$: C, 73.88; H, 8.75.

Found: C, 73.99; H, 8.95.

EXAMPLE 3

A solution of chlorosulfonic acid (2.79 ml) in dichloromethane ($CH_2Cl_2$) (15 ml) was added dropwise to a solution of ethyl (2,5,7,8-tetramethylchroman-2-yl)acetate (2.90 g) in $CH_2Cl_2$ (100 ml) at 0–10° C. over an hour. After stirring at room temperature for 5 hours, the reaction mixture was poured into chilled saturated aqueous sodium hydrogen carbonate (sat. aq. $NaHCO_3$). The separated organic phase was washed with sat. aq. $NaHCO_3$, water, and brine, and dried over $MgSO_4$. After filtration, the filtrate was concentrated under reduced pressure to give 2-ethoxycarbonylmethyl-2,5,7,8-tetramethylchroman-6-sulfonyl chloride as a syrup (3.29 g).

IR (Neat): 1720, 1550 $cm^{-1}$

Reference 11

To a suspension of benzamidine hydrochloride (2.72 g) in acetone (70 ml) was added 1N aqueous sodium hydroxide (1N $N_aOH$) (17.3 ml) under ice-cooling. To the mixture of a solution of 2-ethoxycarbonylmethyl-2,5,7,8-tetramethylchroman-6-sulfonyl chloride (3.25 g) in acetone (15 ml) was added dropwise over 15 minutes under ice-cooling, and stirred at room temperature for 20 hours. Acetone was removed under reduced pressure to give a residue. To the residue was added a mixture of water and AcOEt and the mixture was acidified with 1N HCl. The separated organic phase was washed with water and brine, and dried over $MgSO_4$. After filtration, the filtrate was evaporated and purified by chromatography over silica gel (AcOEt-hexane 50:50 as eluent) to give N-(2-ethoxycarbonylmethyl-2,5,7,8-tetramethylchroman-6-sulfonyl)benzamidine as a glass (1.60 g).

IR (CHCl$_3$): 3450, 3350, 1730, 1630, 1532 cm$^{-1}$ $^1$H-NMR (200 MHz, CDCl$_3$, δ): 1.26 (3H, t, J=7.1 Hz), 1.43 (3H, s), 1.8–2.15 (2H, m), 2.11 (3H, s), 2.6–2.75 (10H, m), 4.15 (2H, q, J=7.1 Hz), 6.23 (1H, br s), 7.35–7.6 (3H, m), 7.75–7.85 (2H, m), 8.14 (1H, br s)

MASS spectrum m/e: 459 (M+H$^+$)

Anal. Calcd. for C$_{24}$H$_{30}$N$_2$O$_5$S: C, 62.86; H. 6.59; N, 6.11.

Found C, 62.78; H, 6.60; N, 6.00.

Reference 12

A solution of N-(2-ethoxycarbonylmethyl-2,5,7,8-tetramethylchroman-6-sulfonyl)benzamidine (1.54 g) in a mixture of ethanol (EtOH) (30 ml) and 1N NaOH (7.05 ml) was stirred at room temperature for 30 hours. EtOH was evaporated under reduced pressure to give a residue. A mixture of AcOEt and 1N HCl was added to the residue. The organic phase was washed with water and brine, and dried over MgSO$_4$. After filtration, the filtrate was concentrated under reduced pressure to give N-(2-carboxymethyl-2,5,7,8-tetramethylchroman-6-sulfonyl)benzamidine as a glass (1.49 g).

IR (CHCl$_3$): 3450, 3350, 1710, 1630, 1535 cm$^{-1}$ $^1$H-NMR (200 MHz, CDCl$_3$, δ) 1.45 (3H, s), 1.75–2.1 (5H, m), 2.5–2.7 (10H, m), 6.40 (1H, br s), 7.3–7.55 (3H, m), 7.75–7.8 (2H, m), 8.12 (1H, br s)

MASS spectrum m/e: 431 (M+H$^+$), 373

Reference 13

A solution of dicyclohexylamine (0.54 g) in AcOEt (1 ml) was added to a solution of N-(2-carboxymethyl-2,5,7,8-tetramethylchroman-6-sulfonyl)benzamidine (1.27 g) in AcOEt (11 ml) at room temperature. Diisopropyl ether (10 ml) was added and the mixture was stirred at room temperature to give N-(2-carboxymethyl-2,5,7,8-tetramethylchroman-6-sulfonyl)benzamidine dicyclohexylamine salt as a solid (1.59 g).

mp: 201–204° C.

IR (Nujol): 3350, 1620, 1550, 1530 cm$^{-1}$ $^1$H-NMR (200 MHz, CDCl$_3$, δ) 1.1–2.9 (28H, m), 1.45 (3H, s), 2.11 (3H, s), 2.60 (3H, s), 2.62 (3H, s), 5.40 (2H, br s), 6.36 (1H, br s), 7.35–7.55 (3H, m), 7.75–7.85 (2H, m), 8.10 (1H, br s)

MASS spectrum m/e: 431 (M+H$^+$ of free)

Anal. Calcd. for C$_{34}$H$_{49}$N$_3$O$_5$S: C, 66.74; H. 8.07; N, 6.87.

Found: C, 66.36; H, 8.29; N, 6.70.

Preparation 7

A solution of ethyl (2,5,7,8-tetramethylchroman-2-yl) acetate (8.00 g) in tetrahydrofuran (THF) (16 ml) was added dropwise to the suspension of lithium aluminum hydride (1.10 g) in THF (40 ml) under reflux. After refluxing for 2 hours, a solution of water (1 ml) in THF (5 ml) was added to the reaction mixture. The insoluble material was filtered off and the filtrate was concentrated under reduced pressure to give a residue. The residue was purified by chromatography over silica gel (AcOEt-hexane 10:90) to give 2-(2,5,7,8-tetramethylchroman-2-yl)ethanol as a solid (5.00 g).

mp: 67–69° C.

IR (Nujol): 3400, 1460 cm$^{-1}$ $^1$H-NMR (200 MHz, CDCl$_3$, δ): 1.30 (3H, s), 1.7–2.0 (4H, m), 2.05 (3H, s), 2.16 (3H, s), 2.20 (3H, s), 2.26 (1H, s), 2.63 (2H, t, J=6.8 Hz), 3.8–4.0 (2H, m), 6.58 (1H, s)

MASS spectrum m/e: 235 (M+H$^+$), 189, 149

Anal. Calcd. for C$_{15}$H$_{22}$O$_2$: C, 76.88; H, 9.46.

Found: C, 76.92; H, 9.61.

Preparation 8

A solution of potassium tert-butoxide (1.92 g) in THF (10 ml) was added dropwise to a solution of 2-(2,5,7,8-tetramethylchroman-2-yl)ethanol (4.00 g) and ethyl bromoacetate (2.00 ml) in THF (20 ml) at 0–10° C. and the mixture was stirred for 30 minutes under same condition. After addition of ethyl bromoacetate (1.90 ml), a solution of potassium tert-butoxide (1.92 g) in THF (10 ml) was added dropwise and the mixture was stirred at 0–10° C. for 30 minutes. This procedure was repeated 3 times. A solution of NaOH (5.0 g) in water (10 ml) was added and heated at 50–55° C. for 5 hours. The mixture was adjusted to pH 3 with 6N hydrochloric acid (6N HCl) and extracted with AcOEt. The organic phase was dried over MgSO$_4$ and concentrated under reduced pressure to give a syrup. A mixture of the syrup and a cation-exchange resin, Amberlyst® 15 (1 g) in MeOH (100 ml) was heated under reflux for 30 hours. After removal of catalyst, the solution was concentrated under reduced pressure to give a syrup. The syrup was purified by chromatography over silica gel (AcOEt-hexane 5:95) to give methyl [2-(2,5,7,8-tetramethylchroman-2-yl)ethoxy]acetate as an oil (3.37 g).

IR (Neat): 1755, 1575 cm$^{-1}$ $^1$H-NMR (200 MHz, CDCl$_3$, δ): 1.30 (3H, s), 1.75–2.1 (4H, m), 2.10 (3H, s), 2.15 (3H, s), 2.19 (3H, s), 2.60 (2H, t, J=6.5 Hz), 3.6–3.85 (2H, m), 3.74 (3H, s), 4.08 (2H, s), 6.55 (1H, s)

MASS spectrum m/e: 307 (M+H$^+$), 279, 217, 149

Anal. Calcd. for C$_{18}$H$_{26}$O$_4$: C, 70.56; H, 8.55.

Found: C, 70.60; H, 8.70.

EXAMPLE 4

2-[2-(Methoxycarbonylmethoxy)ethyl]-2,5,7,8-tetramethylchroman-6-sulfonyl chloride was obtained according to a similar manner to that of Example 3.

IR (Neat): 1752, 1549 cm$^{-1}$ $^1$H-NMR (200 MHz, CDCl$_3$, δ): 1.35 (3H, s), 1.8–2.05 (4H, m), 2.14 (3H, s), 2.60 (3H, s), 2.63 (3H, s), 2.65–2.75 (2H, m), 3.55–3.85 (2H, m), 3.76 (3H, s), 4.09 (2H, s)

Reference 14

N-{2-[2-(Methoxycarbonylmethoxy)ethyl]-2,5,7,8-tetramethylchroman-6-sulfonyl}benzamidine was obtained according to a similar manner to that of Reference 11.

IR (CHCl$_3$): 3420, 3320, 1740, 1625, 1530 cm$^{-1}$ $^1$H-NMR (200 MHz, CDCl$_3$, δ) 1.30 (3H, s), 1.8–2.05 (4H, m), 2.11 (3H, s), 2.61 (3H, s), 2.63 (3H, s), 2.6–2.7 (2H, m), 3.55–3.85 (2H, m), 3.75 (3H, s), 4.08 (2H, s), 6.18 (1H, br s), 7.35–7.6 (3H, m), 7.75–7.85 (2H, m), 8.13 (1H, br s)

MASS spectrum m/e: 489 (M+H$^+$)

Anal. Calcd. for C$_{25}$H$_{32}$N$_2$O$_6$S: C, 61.46; H, 6.60; N, 5.73.

Found C, 61.15; H, 6.72; N, 5.61.

Reference 15

N-{2-[2-(Carboxymethoxy)ethyl]-2,5,7,8-tetramethylchroman-6-sulfonyl}benzamidine was obtained according to a similar manner to that of Reference 12.

IR (CHCl$_3$): 3420, 3330, 3230, 1720, 1623, 1528 cm$^{-1}$ $^1$H-NMR (200 MHz, CDCl$_3$, δ): 1.30 (3H, s), 1.8–2.05 (4H, m), 2.10 (3H, s), 2.5–2.7 (2H, m), 2.60 (3H, s), 2.61 (3H, s), 3.6–3.85 (2H, m), 4.10 (2H, m), 6.32 (1H, br s), 7.35–7.55 (3H, m), 7.75–7.8 (2H, m), 8.12 (1H, br s)

Reference 16

N-{2-[2-(Carboxymethoxy)ethyl]-2,5,7,8-tetramethylchroman-6-sulfonyl}benzamidine dicyclohexylamine salt was obtained according to a similar manner to that of Reference 13.

mp: 184–186° C.

IR (Nujol): 3380, 1622 cm$^{-1}$ $^1$H-NMR (200 MHz, CDCl$_3$, δ): 1.28 (3H, s), 2.09 (3H, s), 2.59 (3H, s), 2.61 (3H, s), 3.84 (2H, s), 7.11 (1H, br s), 7.25–7.55 (3H, m); 7.75–7.85 (2H, m), 8.01 (1H, br s)

MASS spectrum m/e: 475 (M+H$^+$ of free)

Anal. Calcd. for C$_{36}$H$_{53}$N$_3$O$_6$S: C, 65.92; H, 8.14; N, 6.41.

Found: C, 65.65; H, 8.39; N, 6.29.

Preparation 9

According to the method of D. Murali and G. S. Krishna Rao (Synthesis, 1987, 254–56), 5,6,7,8-tetrahydro-3-methyl-1-naphthyl acetate was synthesized from cyclohexanone and triethyl 3-methyl-4-phosphonocrotonate.

Preparation 10

A solution of 5,6,7,8-tetrahydro-3-methyl-1-naphthyl acetate (11.00 g) and NaOH (6.50 g) in a mixture of water (50 ml) and MeOH (150 ml) was refluxed for 5 hours. MeOH was removed under reduced pressure to give a residue. AcOEt was added to the residue and c-HCl was added dropwise under ice-cooling. The organic phase was washed with brine and dried over MgSO$_4$. After filtration, the filtrate was concentrated under reduced pressure to give 5,6,7,8-tetrahydro-3-methyl-1-naphthol as a solid (8.19 g).

mp 94–95° C. (hexane)

IR (Nujol): 3450–3350, 1623, 1582 cm$^{-1}$ $^1$H-NMR (200 MHz, CDCl$_3$, δ) 1.65–1.9 (4H, m), 2.23 (3H, s), 2.58 (2H, t, J=6.0 Hz), 2.70 (2H, t, J=5.8 Hz), 4.61 (1H, s), 6.44 (1H, s), 6.51 (1H, s)

MASS spectrum m/e: 163 (M+H$^+$)

Preparation 11

A suspension of boric acid (5.88 g) in glycerol (20 ml) was heated at 170° C. for 30 minutes. Temperature of the reaction mixture was lowered at 155° C. and 5,6,7,8-tetrahydro-3-methyl-1-naphthol (5.00 g) was added dropwise over 10 minutes. After 15 minutes, hexamethylenetetramine (4.35 g) was added dropwise below 180° C. and stirred at 170° C. for 30 minutes. The mixture was cooled to 110° C. and 24% aqueous sulfuric acid (20 ml) was added. The mixture was steam distilled and AcOEt was added to the distillate. The organic phase was washed with brine and dried over MgSO$_4$. After filtration, the filtrate was concentrated under reduced pressure to give 5,6,7,8-tetrahydro-1-hydroxy-3-methylnaphthalene-2-carbaldehyde as a solid (2.15 g). A pure sample was obtained by recrystallization from EtOH-H$_2$O.

mp: 74–75° C. (EtOH-H$_2$O)

IR (Nujol): 1625 cm$^{-1}$ $^1$H-NMR (200 MHz, CDCl$_3$, δ) 1.7–1.85 (4H, m), 2.52 (3H, s), 2.6–2.75 (4H, m), 6.44 (1H, s), 10.20 (1H, s), 12.35 (1H, s)

MASS spectrum m/e: 191 (M+H$^+$), 175

Anal. Calcd. for C$_{12}$H$_{14}$O$_2$: C, 75.76; H, 7.42.

Found C, 75.96; H, 7.55.

Preparation 12

Ethyl (7,8,9,10-tetrahydro-2,5-dimethyl-2H-naphtho-[2,1-e]pyran-2-yl)acetate was obtained according to a similar manner to that of Preparation 5.

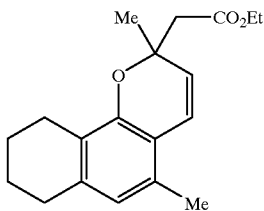

IR (Neat): 1735, 1605 cm$^{-1}$ $^1$H-NMR (200 MHz, CDCl$_3$, δ) 1.23 (3H, t, J=7.1 Hz), 1.56 (3H, s), 1.65–1.8 (4H, m), 2.23 (3H, s), 2.55–2.8 (6H, m), 4.11 (2H, q, J=7.1 Hz), 5.69 (1H, d, J=10.0 Hz), 6.46 (1H, s), 6.53 (1H, d, J=10.0 Hz)

MASS spectrum m/e: 301 (M+H$^+$), 213 (M$^+$—CH$_2$CO$_2$Et)

Anal. Calcd. for C$_{19}$H$_{24}$O$_3$: C, 75.97; H, 8.05.

Found: C, 75.54; H, 8.13.

Preparation 13

Ethyl (3,4,7,8,9,10-hexahydro-2,5-dimethyl-2H-naphtho-[2,1-e]pyran-2-yl)acetate was obtained according to a similar manner to that of Preparation 6.

IR (Neat): 1730, 1578 cm$^{-1}$ $^1$H-NMR (200 MHz, CDCl$_3$, δ): 1.26 (3H, t, J=7.1 Hz), 1.42 (3H, s), 1.7–1.75 (4H, m), 1.8–2.15 (2H, m), 2.16 (3H, s), 2.5–2.65 (8H, m), 4.14 (2H, q, J=7.1 Hz), 6.50 (1H, s)

MASS spectrum m/e: 303 (M+H$^+$), 215 (M$^+$—CH$_2$CO$_2$Et)

Anal. Calcd. for C$_{19}$H$_{26}$O$_3$: C, 75.46; H, 8.67.

Found C, 75.32; H, 8.82.

EXAMPLE 5

2-Ethoxycarbonylmethyl-3,4,7,8,9,10-hexahydro-2,5-dimethyl-2H-naphtho[2,1-e]pyran-6-sulfonyl chloride was obtained according to a similar manner to that of Example 3.

IR (Neat): 1730, 1705 cm$^{-1}$

Reference 17

N-(2-Ethoxycarbonylmethyl-3,4,7,8,9,10-hexahydro-2,5-dimethyl-2H-naphtho[2,1-e]pyran-6-sulfonyl)benzamidine was obtained according to a similar manner to that of Reference 11.

IR (CHCl$_3$): 3450, 3350, 1725, 1630, 1533 cm$^{-1}$ $^1$H-NMR (200 MHz, CDCl$_3$, δ): 1.26 (3H, t, J=7.1 Hz), 1.43 (3H, s), 1.6–1.75 (4H, m), 1.8–2.3 (2H, m), 2.6–2.7 (9H, m), 3.27 (2H, br s), 4.14 (2H, q, J=7.1 Hz), 6.22 (1H, br s), 7.35–7.6 (3H, m), 7.75–7.8 (2H, m), 8.16 (1H, br s)

MASS spectrum m/e: 485 (M+H$^+$), 397

Anal. Calcd. for C$_{26}$H$_{32}$N$_2$O$_5$S: C, 64.44; H. 6.65; N, 5.78.

Found: C, 64.27; H, 6.64; N, 5.57.

Reference 18

N-(2-Carboxymethyl-3,4,7,8,9,10-hexahydro-2,5-dimethyl-2H-naphtho[2,1-e]pyran-6-sulfonyl)benzamidine was obtained according to a similar manner to that of Reference 12.

IR (CHCl$_3$): 3420, 3320, 1710, 1632, 1530 cm$^{-1}$ $^1$H-NMR (200 MHz, CDCl$_3$, δ): 1.45 (3H, s), 1.68 (4H, br s), 1.85–2.2 (2H, m), 2.6–2.75 (2H, m), 2.61 (3H, s), 2.67 (2H, s), 6.27 (1H, br s), 7.3–7.6 (3H, m), 7.75–7.8 (2H, m), 8.15 (1H, br s)

MASS spectrum m/e: 457 (M+H$^+$), 391

Reference 19

A solution of dicyclohexylamine (0.22 g) in AcOEt (1 ml) was added to a solution of N-(2-carboxymethyl-3,4,7,8,9, 10-hexahydro-2,5-dimethyl-2H-naphtho[2,1-e]pyran-6-sulfonyl)benzamidine (0.55 g) in AcOEt (4 ml) and the mixture was stirred at room temperature to give N-(2-carboxymethyl-3,4,7,8,9,10-hexahydro-2,5-dimethyl-2H-naphtho[2,1-e]pyran-6-sulfonyl)benzamidine dicyclohexylamine salt as a solid (0.66 g).

mp: 188–190° C.

IR (Nujol): 3370, 1620, 1530 cm$^{-1}$

MASS spectrum m/e: 457 (M+H$^+$ of free)

Anal. Calcd. for $C_{36}H_{51}N_3O_5S$: C, 67.78; H, 8.06; N, 6.59.

Found: C, 67.37; H, 8.26; N, 6.36.

What is claimed is:

1. A linker of the formula (I):

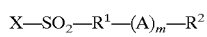
(I)

wherein:

$R^1$ is a group of the formula (B):

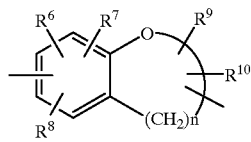
(B)

wherein:

$R^6$, $R^7$, $R^8$ and $R^9$, which are the same or different, is each lower alkyl;

$R^{10}$ is hydrogen;

n is an integer of 1 to 3;

$R^2$ is a group which forms a chemical bond to a resin which is optionally protected by a protective group;

A is lower alkylene or a group of the formula:

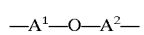

wherein $A^1$ and $A^2$ are each lower alkylene;

X is a leaving group; and m is an integer of 0 or 1;

or a salt thereof.

2. The linker of claim 1, wherein $R^1$ is a group of the formula (B), wherein n is an integer of 3;

$R^2$ is a group which forms a chemical bond to a resin which is optionally protected by a protective group;

A is $(C_1-C_4)$ alkylene or a group of the formula:

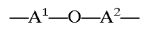

wherein $A^1$ and $A^2$ are each $(C_1-C_4)$ alkylene;

X is halogen; and m is an integer of 0 or 1.

3. The linker of claim 2, wherein $R^1$ is a group of the formula:

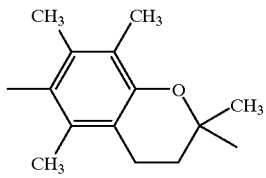

$R^2$ is a group which forms a chemical bond to a resin which is optionally protected by a protective group;

A is methylene or $-(CH_2)_2-O-CH_2-$;

X is chloro; and m is an integer of 1.

4. The linker of claim 1, wherein $R^1$ is a group of the formula (B) wherein n is an integer of 3;

$R^2$ is a group which forms a chemical bond to a resin which is optionally protected by a protective group;

A is $(C_1-C_4)$ alkylene or a group of the formula:

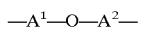

wherein $A^1$ and $A^2$ are each $(C_1-C_4)$ alkylene;

X is halogen; and m is an integer of 0 or 1.

5. The linker of claim 4, wherein $R^1$ is a group of the formula:

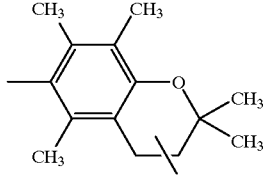

$R^2$ is a group which forms a chemical bond to a resin which is optionally protected by a protective group;

X is chloro; and m is an integer of 0; or $R^1$ is a group of the formula:

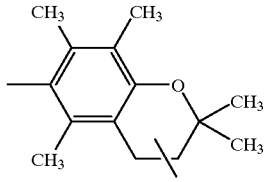

$R^2$ is a group which forms a chemical bond to a resin which is optionally protected by a protective group;

A is methylene or $-(CH_2)_2-O-CH_2-$;

X is chloro; and m is an integer of 1.

6. The linker compound of claim 1, wherein
R$^1$ is a group of the formula:

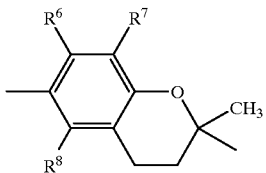

wherein:
R$^6$, R$^7$ and R$^8$ are each lower alkyl;
R$^2$ is a group which forms a chemical bond to a resin which is optionally protected by a protective group;
A is (C$_1$–C$_4$) alkylene or a group of the formula:

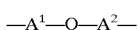

wherein A$^1$ and A$^2$ are each (C$_1$–C$_4$) alkylene;
X is a leaving group; and
m is an integer of 0 or 1.

7. A linker of the formula (I):

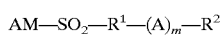  (I)

wherein:

R$^1$ is a group of the formula (B)

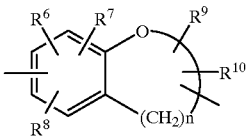  (B)

wherein:
AM is a directly bonded amine compound;
R$^6$, R$^7$, R$^8$ and R$^9$, which are the same or different, is each lower alkyl;
R$^{10}$ is hydrogen; and
n is an integer of 1 to 3;
R$^2$ is a group which forms a chemical bond to a resin which is optionally protected by a protective group;
A is lower alkylene or a group of the formula:

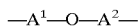

wherein A$^1$ and A$^2$ are each lower alkylene,
X is a leaving group; and
m is an integer of 0 or 1;
or a salt thereof.

* * * * *

UNITED STATES PATENT AND TRADEMARK OFFICE
CERTIFICATE OF CORRECTION

PATENT NO.    : 6,225,480 B1
DATED         : May 1, 2001
INVENTOR(S)   : Tanaka et al.

It is certified that error appears in the above-identified patent and that said Letters Patent is hereby corrected as shown below:

<u>Title page,</u>
Item [30], the Foreign Application Priority Data is incorrect, item [30] should read as follows:

-- [30]     Foreign Application Priority Data

Dec. 30, 1996     (AU)................................................ PO4405 --

Signed and Sealed this

Sixth Day of November, 2001

Attest:

NICHOLAS P. GODICI
*Attesting Officer*     *Acting Director of the United States Patent and Trademark Office*